United States Patent [19]

Higashii et al.

[11] Patent Number: 5,658,489

[45] Date of Patent: Aug. 19, 1997

[54] DIPHENYLACETYLENE COMPOUND, PROCESS FOR PREPARING THE SAME AND LIQUID CRYSTAL COMPOSITION AND ELEMENT COMPRISING THE SAME

[75] Inventors: Takayuki Higashii, Yokohama; Yukari Fujimoto, Osaka; Masayoshi Minai, Moriyama; Tsutomu Matsumoto, Kyoto, all of Japan

[73] Assignee: Sumitomo Chemical Company, Limited, Osaka, Japan

[21] Appl. No.: 322,332

[22] Filed: Oct. 13, 1994

[30] Foreign Application Priority Data

| Oct. 13, 1993 | [JP] | Japan | 5-255653 |
| Oct. 21, 1993 | [JP] | Japan | 5-263504 |
| Jun. 1, 1994 | [JP] | Japan | 6-120234 |
| Jun. 30, 1994 | [JP] | Japan | 6-149674 |
| Aug. 4, 1994 | [JP] | Japan | 6-183460 |
| Aug. 9, 1994 | [JP] | Japan | 6-187626 |

[51] Int. Cl.$^6$ .................. C09K 19/52; C07D 239/00; C07D 211/72; C07C 25/13
[52] U.S. Cl. .................. 252/299.01; 252/299.6; 252/299.61; 544/242; 544/298; 544/335; 544/336; 546/339; 546/345; 546/346; 568/647; 570/127
[58] Field of Search .................. 252/299.6, 299.01, 252/299.5, 299.61; 544/242, 298, 334, 335, 336; 546/339, 345, 346; 570/127; 568/647

[56] References Cited

U.S. PATENT DOCUMENTS

| 5,047,169 | 9/1991 | Shibata et al. | 252/299.6 |
| 5,164,114 | 11/1992 | Kurmeier et al. | 252/299.61 |
| 5,171,473 | 12/1992 | Buchecker et al. | 252/299.61 |
| 5,308,538 | 5/1994 | Weber et al. | 252/299.61 |
| 5,314,640 | 5/1994 | Yamada et al. | 252/299.6 |
| 5,338,481 | 8/1994 | Wu et al. | 252/299.01 |
| 5,356,562 | 10/1994 | Greenfield et al. | 252/299.63 |
| 5,399,292 | 3/1995 | Buchecker et al. | 252/299.63 |

FOREIGN PATENT DOCUMENTS

| 0361532 | 12/1986 | European Pat. Off. |
| 0249933 | 12/1987 | European Pat. Off. |
| 63-502284 | 9/1988 | Japan |
| 63-253063 | 10/1988 | Japan |
| 421640 | 5/1990 | Japan |
| 2121936 | 5/1990 | Japan |
| 3176437 | 7/1991 | Japan |

OTHER PUBLICATIONS

Ikeda et al., "Complete 1, 3 Asymmetric Induction in the Reactions of Allenylboronic Acid with B-hydroxy Ketones", Tetrahedron Letters, 27, 1175–1178, 1986.

Chen et al., "Palladium catalyzed reaction of Phenylalkanesulfonates with Alkynes and Alkenes", Tetrahedron Letters 27, 1171–1174. 1986.

Database WPI, Derwent Publications Ltd. AN 93–383033 (1993) (abstract).

Database WPI, Derwent Publications Ltd., AN 86–269531 (1985) (abstract).

*Primary Examiner*—Shean C. Wu
*Attorney, Agent, or Firm*—Birch, Stewart, Kolasch & Birch, LLP

[57] ABSTRACT

A diphenylacetylene compound of the formula [1]:

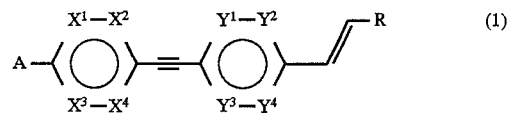

wherein R is a $C_1$–$C_{12}$ alkyl group, a $C_2$–$C_{12}$ alkenyl group or a $C_2$–$C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom;

A is a hydrogen atom, a fluorine atom, a trifluoromethyl group, a trifluoromethoxy group, a cyano group, a 4-$R^1$-(cycloalkyl) group, 4-$R^1$-(cycloalkenyl) group or a $R^1$—$(O)_m$ group in which $R^1$ is a $C_1$–$C_{12}$ alkyl group, a $C_2$–$C_{12}$ alkenyl group or a $C_2$–$C_{12}$ alkynyl group; and m is 0 or 1, which has an excellent anisotropy of refractive index and a low viscosity and is useful as a component of a liquid crystal composition.

20 Claims, No Drawings

DIPHENYLACETYLENE COMPOUND, PROCESS FOR PREPARING THE SAME AND LIQUID CRYSTAL COMPOSITION AND ELEMENT COMPRISING THE SAME

BACKGROUND OF THE INVENTION

1. Field of the Invention

The present invention relates to a diphenylacetylene (hereinafter referred to as "tolan") compound which is useful as a component of a liquid crystal composition, a process for preparing said tolan compound and a liquid crystal composition comprising said tolan compound and a liquid crystal element comprising said liquid crystal composition.

2. Description of the Related Art

In these years, it is inevitable to improve performances of a liquid crystal display element with the visitation of information oriented society. To increase a response speed and achieve high quality of the liquid crystal element, a liquid crystal material which is excellent in an anisotropy of refractive index among properties of the liquid crystal composition is required.

However, hitherto, a liquid crystal material having a sufficient anisotropy of refractive index has not been found.

SUMMARY OF THE INVENTION

An object of the present invention is provide a low viscosity tolan compound which is excellent in an anisotropy of refractive index and is suitable as a liquid crystal material.

Another object of the present invention is to provide a process for preparing said tolan compound, which process is industrially advantageous.

A further object of the present invention is to provide a novel compound which is useful as a starting material in the preparation of the tolan compound of the present invention.

A yet another object of the present invention is to provide a liquid crystal composition comprising said tolan compound.

A yet further object of the present invention is to provide a liquid crystal element comprising said liquid crystal composition.

According to a first aspect of the present invention, there is provided a tolan compound of the formula [1]:

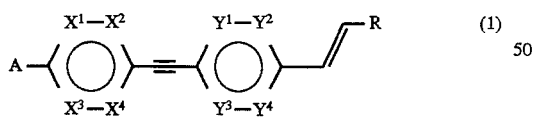

wherein R is a $C_1-C_{12}$ alkyl group, a $C_2-C_{12}$ alkenyl group or a $C_2-C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom;

A is a hydrogen atom, a fluorine atom, a trifluoromethyl group, a trifluoromethoxy group, a cyano group, a 4-$R^1$-(cycloalkyl) group, 4-$R^1$-(cycloalkenyl) group or a $R^1$—(O)$_m$ group in which $R^1$ is a $C_1-C_{12}$ alkyl group, a $C_2-C_{12}$ alkenyl group or a $C_2-C_{12}$ alkynyl group; and m is 0 or 1.

According to a second aspect of the present invention, there is provided a process for preparing a tolan compound of the formula [1] comprising reacting an aromatic compound of the formula [2]:

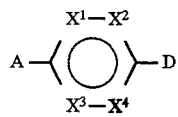

wherein A, $X^1$, $X^2$, $X^3$ and $X^4$ are the same as defined above, and D is a halogen atom or —OSO$_2$R' in which R' is a lower alkyl group having 1 to 4 carbon atoms which may be substituted by a fluorine atom or a $C_1-C_4$ alkyl, $C_1-C_4$ alkoxy or halogen substituted or unsubstituted phenyl group with an ethynyl aromatic derivative of the formula [3]

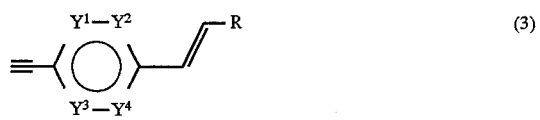

wherein R, $Y^1$, $Y^2$, $Y^3$ and $Y^4$ are the same as defined above in the presence of a metal catalyst and a base.

According to a third aspect of the present invention, there is provided a process for preparing a tolan compound of the formula [1] comprising reacting a tolan derivative of the formula [10]:

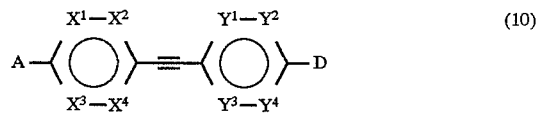

wherein A, D, $X^1$, $X^2$, $X^3$, $X^4$, $Y^1$, $Y^2$, $Y^3$ and $Y^4$ are the same as defined above with a boron compound of the formula [6]:

wherein R is the same as defined above, and each $R^5$ is a hydroxyl group, a straight, branched or cyclic alkyl group having 1 to 15 carbon atoms or a straight, branched or cyclic alkoxy group having 1 to 15 carbon atoms, or two $R^5$ groups together form a straight, branched or cyclic alkylene group having 2 to 30 carbon atoms, a straight, branched or cyclic alkylenedioxy group having 2 to 30 carbon atoms or a benzodioxy group in the presence of a metal catalyst and a base.

According to a fourth aspect of the present invention, there is provided a process for preparing a tolan compound of the formula [1] comprising reacting an ethynyl aromatic compound of the formula [11]:

wherein A, $X^1$, $X^2$, $X^3$ and $X^4$ are the same as defined above with an aromatic derivative of the formula [12]:

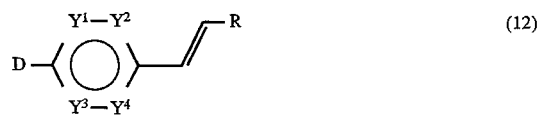

wherein D, R, $Y^1$, $Y^2$, $Y^3$ and $Y^4$ are the same as defined above in the presence of a metal catalyst and a base.

According to a fifth aspect of the present invention, there are provided an ethynyl aromatic derivative of the formula (3):

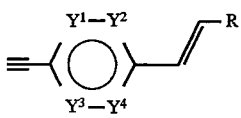

wherein R, $Y^1$, $Y^2$, $Y^3$ and $Y^4$ are the same as defined above, and a carbinol derivative of the formula (7):

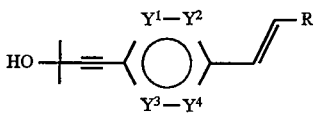

wherein R, $Y^1$, $Y^2$, $Y^3$ and $Y^4$ are the same as defined above.

According to a sixth aspect of the present invention, there is provided a process for preparing an ethynyl aromatic derivative of the formula [3] comprising treating a carbinol derivative of the formula [7]:

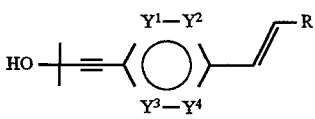

wherein R, $Y^1$, $Y^2$, $Y^3$ and $Y^4$ are the same as defined above with a base.

According to a seventh aspect of the present invention, there is provided a liquid crystal composition comprising the tolan compound [1] of the present invention.

According to an eighth aspect of the present invention, there is provided a liquid crystal element comprising the liquid crystal composition of the present invention.

DETAILED DESCRIPTION OF THE INVENTION

The tolan compound of the formula [1] of the present invention can be prepared by reacting an aromatic compound of the formula [2]:

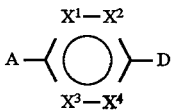

wherein A, D, $X^1$, $X^2$, $X^3$ and $X^4$ are the same as defined above with an ethynyl aromatic derivative of the formula [3]

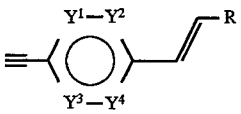

wherein R, $Y^1$, $Y^2$, $Y^3$ and $Y^4$ are the same as defined above in the presence of a metal catalyst and a base.

In the above reaction for synthesizing the tolan compound [1] from the aromatic compound [2] and the ethynyl aromatic derivative [3], an amount of the ethynyl aromatic derivative [3] is usually 0.9 to 3 times equivalents, preferably 1 to 2 times equivalents to the ethynyl aromatic derivative [3]. While it is possible to use the ethynyl aromatic derivative [3] in an excessive amount, it is preferable to use the aromatic compound [2] in an excessive amount since the ethynyl aromatic derivative [3] is generally more expensive than the aromatic compound [2].

As the metal catalyst, a palladium catalyst, a nickel catalyst, a rhodium catalyst and a copper catalyst are exemplified. Specific examples of the palladium catalyst are palladium chloride, palladium acetate, triphenylphosphine palladium complex, palladium on carbon, and the like. Examples of the nickel and rhodium catalysts are the above compounds of the palladium catalyst in which palladium is replaced by nickel or rhodium. Specific examples of the copper catalyst are cuprous or cupric halides such as cuprous iodide, cupric iodide, cuprous bromide, cupric bromide, cuprous chloride and cupric chloride, cuprous or cupric oxide, cuprous or cupric cyanide, and the like. They may be used independently or a mixture of two or more catalysts comprising the same metal or different metals. An example of the mixture of the catalysts comprising the different metals is a palladium catalyst-copper catalyst system, in particular, a triphenylphosphine palladium complex-cuprous or -cupric halide system. Among them, the palladium catalysts and the palladium catalyst-copper catalyst system are preferred.

An amount of the metal catalyst is usually from 0.001 to 0.1 time equivalent to the ethynyl aromatic derivative [3].

In the above reaction, it may be preferable to use an promoter such as a trivalent phosphorus compound or a trivalent arsenic compound. An example of the promoter is a compound of the formula [4]:

wherein Y is a phosphorus atom or an arsenic atom, $R^2$, $R^3$ and $R^4$ are independently an alkyl group, an aryl group, an alkoxy group, an aryloxy group or a halogen atom.

Examples of the compound [4] are tri-n-butylphosphine, triphenylphosphine, tri-o-tolylphosphine, tri-o-tolylphosphite, phosphorus trichloride, triphenylarsine, and the like.

An amount of the phosphorus or arsenic compound is usually from 0.5 to 50 times equivalents, preferably from 2 to 30 times equivalents to the metal catalyst.

Examples of the base are a carbonate, carboxylic acid salt, alkoxide or hydroxide of an alkali metal, and an organic base such as a primary amine (e.g. butylamine, etc.) and a secondary or tertiary amine (e.g. diethylamine, triethylamine, diisopropylethylamine, tri-n-butylamine, tetramethylethylenediamine, dimethylaniline, morpholine, N-methylmorpholine, pyrrolidine, N-methylpyrrolidine, piperidine, N-methylpiperidine, and the like. Among them, the secondary and tertiary amines are preferred.

An amount of the base is usually from 1 to 5 times equivalents to the ethynyl aromatic derivative [3].

If necessary, a solvent may be used. Examples of the solvent are toluene, pyridine, picoline, acetonitrile, tetrahydrofuran, dimethylformamide, hexamethylphosphorylamide, N-methylpyrrolidine, methanol, and the like.

The above organic base may be used also as a solvent.

An amount of the solvent is not limited.

Usually, the above reaction is carried out in an atmosphere of an inert gas such as nitrogen, argon, etc.

An yield of the desired compound can be increased by elevating a reaction temperature. But, at a too high temperature, a by-product may be formed. Then, a reaction temperature is preferably from 15° to 160° C., more preferably from 30° to 140° C.

After the completion of the reaction, the tolan compound [1] can be isolated from the reaction mixture by a conventional method such as extraction, distillation, recrystallization, etc. If required, the tolan compound [1] can be purified by a conventional method such as column chromatography, recrystallization, etc.

The ethynyl aromatic derivative [3] can be prepared by reacting a carbinol compound of the formula [5]:

 (5)

wherein D, $Y^1$, $Y^2$, $Y^3$ and $Y^4$ are the same as defined above with a boron compound of the formula [6]:

$(R^5)_2B-CH=CH-R$ (6)
(trans)

wherein R and $R^5$ are the same as defined above in the presence of a metal catalyst and a base to obtain a carbinol derivative of the formula [7]:

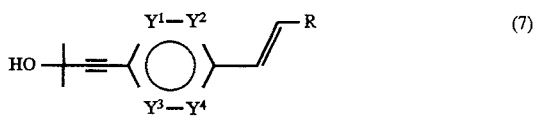 (7)

wherein R, $Y^1$, $Y^2$, $Y^3$ and $Y^4$ are the same as defined above, and treating the carbinol derivative [7] with a base.

Herein, the carbinol compound [5] can be synthesized by the following processes:

(1) When D is a halogen atom:

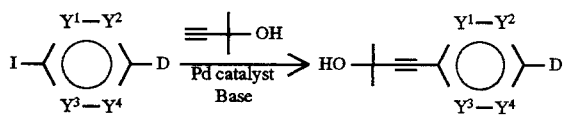

(2) When D is $SO_2R'$:

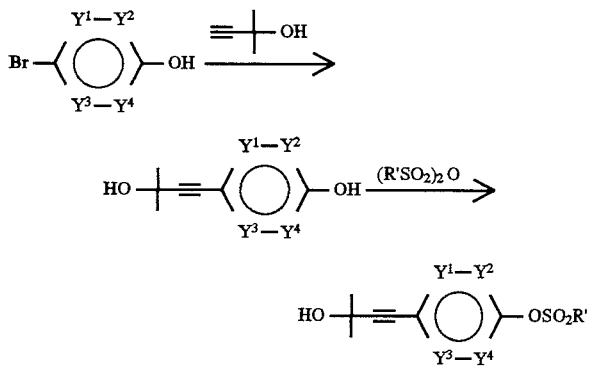

The boron compound [6] which is the other starting material, can be prepared, for example, by the following process:

$HC\equiv C-R[8]+(R^6)_2BH[9]\rightarrow (R^{5'})_2B-CH=CH-R$ (trans) [6']

wherein R is the same as defined above, $R^{5'}$ is the same as $R^5$ except a hydroxyl group.

In the reaction between the alkyne compound [8] and the boron derivative [9], examples of the boron derivative [9] are dialkylboranes (e.g. dicyclohexylborane, disiamylborane, diisopinocamphenylborane, 9-borabicyclo [3.3.1]nonane, etc.), dialkoxyboranes (e.g. diisopropyloxyborane, dimethoxyborane, etc.), catecholborane, and the like.

An amount of the alkyne compound [8] is usually from 0.5 to 10 times equivalent, preferably from 0.5 to 2 times equivalent to the boron derivative [9].

The above reaction is carried out in the presence or absence of a solvent. When the solvent is used, tetrahydrofuran, diethylether, dioxane, acetonitrile, toluene, dichloromethane, dimethylformamide, and the like can be used. An amount of the solvent is not limited.

The reaction temperature of the above reaction is usually from $-20°$ to $+150°$ C., preferably from 0° to 100° C.

The boron compound of the formula [6] in which $R^5$ is a hydroxyl group can be prepared by hydrolyzing the compound of the formula [6'] which is obtained by the above reaction.

In the reaction for preparing the carbinol derivative [7] from the carbinol compound [5] and the boron compound [6], an amount of the boron compound [6] is usually from 0.9 to 10 times equivalent, preferably 1 to 2 times equivalent to the carbinol compound [5]. While it is possible to use an excessive amount of the carbinol compound [5], it is preferable to use the boron compound [6] in the excessive amount since the carbinol compound [5] is generally more expensive than the boron compound [6].

As the metal catalyst, a palladium catalyst, a nickel catalyst, a rhodium catalyst and a copper catalyst are exemplified. Specific examples of the palladium catalyst are palladium chloride, palladium acetate, triphenylphosphine palladium complex, palladium on carbon, and the like. Examples of the nickel and rhodium catalysts are the above compounds of the palladium catalyst in which palladium is replaced by nickel or rhodium. Specific examples of the copper catalyst are cuprous or cupric halides such as cuprous iodide, cupric iodide, cuprous bromide, cupric bromide, cuprous chloride and cupric chloride, cuprous or cupric oxide, cuprous or cupric cyanide, and the like. They may be used independently or a mixture of two or more catalysts comprising the same metal or different metals. An example of the mixture of the catalysts comprising the different metals is a palladium catalyst-copper catalyst system, in particular, a triphenylphosphine palladium complex-cuprous or -cupric halide system. Among them, the palladium catalysts and the palladium catalyst-copper catalyst system are preferred.

An amount of the metal catalyst are usually from 0.001 to 0.1 equivalent to the carbinol compound [5].

In the above reaction, it may be preferable to use an promoter such as a trivalent phosphorus compound or a trivalent arsenic compound. An example of the promoter is the compound of the above formula [4], in particular, tri-n-butylphosphine, triphenylphosphine, tri-o-tolylphosphine, tri-o-tolylphosphite, phosphorus trichloride, triphenylarsine, and the like.

An amount of the phosphorus or arsenic compound [4] is usually from 0.5 to 50 times equivalents, preferably from 2 to 30 times equivalents to the metal catalyst.

The reaction can be accelerated by the use of a base. Examples of the base are a carbonate, carboxylic acid salt, alkoxide or hydroxide of an alkali metal, and an organic base such as a primary amine (e.g. butylamine, etc.) and a secondary or tertiary amine (e.g. diethylamine, triethylamine, diisopropylethylamine, tri-n-butylamine, tetramethylethylenediamine, dimethylaniline, morpholine, N-methylmorpholine, pyrrolidine, N-methylpyrrolidine, piperidine, N-methylpiperidine, and the like. Among them, alkali metal hydroxides such as sodium hydroxide and potassium hydroxide, alkali metal carbonates or hydrogencarbonates such as potassium carbonate, sodium carbonate, potassium hydrogencarbonate and sodium hydrogencarbonate, and alkali metal alkoxides such as sodium ethoxide and sodium methoxide are preferred.

An amount of the base is usually from 1 to 5 times equivalent to the carbinol compound [5].

If desired, a solvent may be used. Examples of the solvent are water, methanol, ethanol, isopropanol, tert.-butanol, acetonitrile, tetrahydrofuran, dimethylformamide, hexamethylphosphorylamide, N-methylpyrrolidone, benzene, toluene and the like. An amount of the solvent is not limited.

A reaction temperature in the above reaction is usually from −20° to +150° C., preferably from 20° to 110° C.

After the completion of the reaction, the carbinol derivative [7] can be isolated from the reaction mixture by a conventional method such as extraction, distillation, recrystallization, etc. If required, the carbinol derivative [7] can be purified by a conventional method such as column chromatography, recrystallization, etc.

Next, a reaction for preparing the ethynyl aromatic derivative [3] by treating the carbinol derivative [7] with the base will be explained.

As the base, there may be used an alkali metal, an alkaline earth metal, their carbonates, carboxylic acid salts, alkoxides, hydride or hydroxide, and an organic base such as 1,8-diazabicyclo[5.4.0]undec-7-ene, triethylamine, diisopropylethylamine, tri-n-butylamine, tetramethylethylenediamine, dimethylaniline, N-methylmorpholine, N-methylpiperidine, and the like. Preferred examples of the base are hydroxides such as sodium hydroxide and potassium hydroxide, and alkoxides such as sodium ethoxide and sodium methoxide.

An amount of the base is usually from 0.02 to 50 times equivalent to the carbinol derivative [7].

If necessary, a solvent may be used. Examples of the solvent are n-butanol, tert.-butanol, methyl tert.-butyl ether, hexane, chlorobenzene, dichlorobenzene, benzene, toluene, xylene, tetrahydrofuran, cyclohexane, decane, dimethylformamide, hexamethylphosphorylamide, N-methylpyrrolidone, dimethylsulfoxide, and the like. An amount of the solvent is not limited.

A reaction temperature in this reaction is usually from 20° to 190° C., preferably from 40° to 150° C.

A reaction time is not critical.

Since acetone is by-produced as the reaction proceeds, the reaction can be effectively accelerated by the removal of acetone in the course of the reaction at intervals or continuously.

After the completion of the reaction, the ethynyl aromatic derivative [3] can be isolated from the reaction mixture by a conventional method such as extraction, distillation, etc. If required, the ethynyl aromatic derivative [3] can be purified by a conventional method such as distillation, column chromatography, etc.

The aromatic compound [2] may be a commercially available compound or prepared by an analogous process to the preparation of such commercially available compound. Alternatively, the aromatic compound can be prepared by the following process:

(1) When D is —OSO$_2$R':

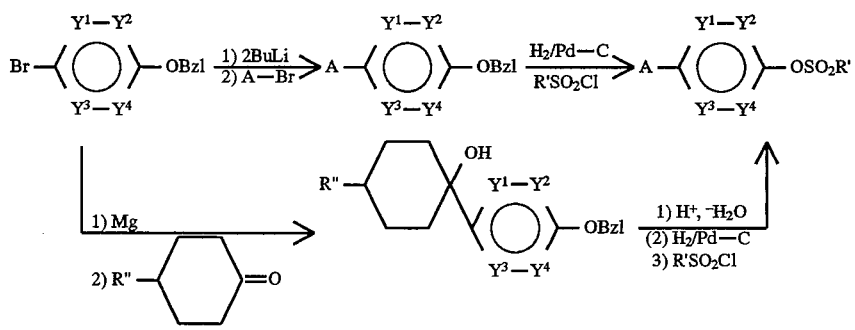

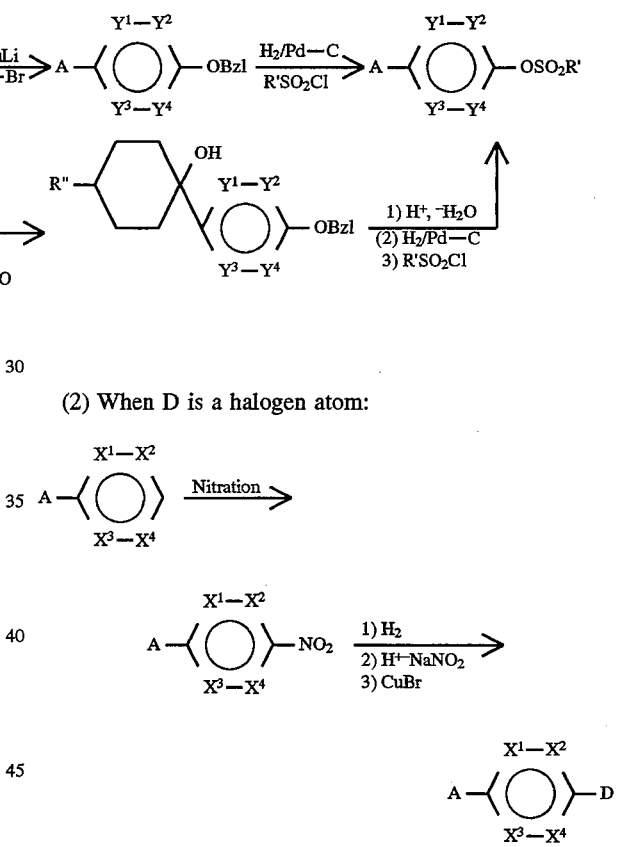

(2) When D is a halogen atom:

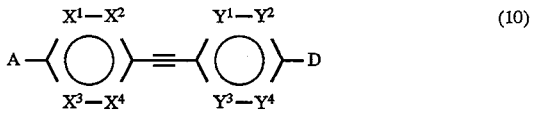

The tolan compound [1] of the present invention can be prepared by reacting a tolan derivative of the formula [10]:

$$A-\!\!\left\langle\!\!\begin{array}{c}X^1-X^2\\\bigcirc\\X^3-X^4\end{array}\!\!\right\rangle\!\!-\!\!\equiv\!\!-\!\!\left\langle\!\!\begin{array}{c}Y^1-Y^2\\\bigcirc\\Y^3-Y^4\end{array}\!\!\right\rangle\!\!-D \quad (10)$$

wherein A, D, $X^1$, $X^2$, $X^3$, $X^4$, $Y^1$, $Y^2$, $Y^3$ and $Y^4$ are the same as defined above with the boron compound of the formula [6] in the presence of a metal catalyst and a base.

The raw material tolan derivative [10] may be prepared by the following process:

(1) When D is a halogen atom:

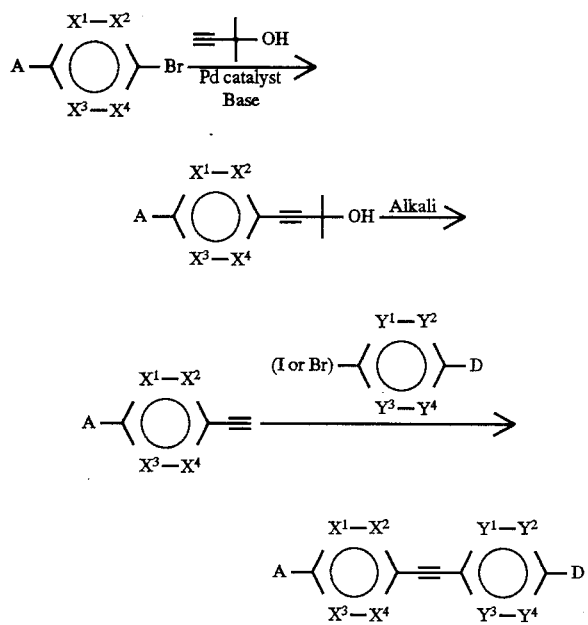

(2) When D is —OSO₂R':

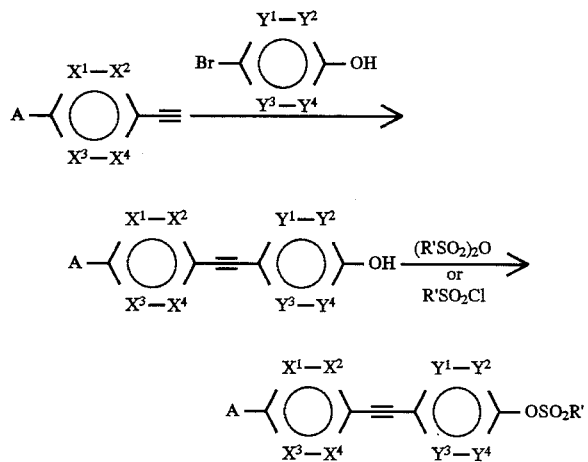

In the reaction for synthesizing the tolan compound [1] from the tolan derivative [10] and the boron compound [6], an amount of the boron compound [6] is usually from 0.9 to 10 times equivalent, preferably from 1 to 2 times equivalent to the tolan derivative [10]. While it is possible to use an excessive amount of the tolan derivative [10], it is preferable to use the boron compound [6] in the excessive amount since the tolan derivative [10] is generally more expensive than the boron compound [6].

As the metal catalyst, a palladium catalyst, a nickel catalyst, a rhodium catalyst and a copper catalyst are exemplified. Specific examples of the palladium catalyst are palladium chloride, palladium acetate, triphenylphosphine palladium complex, palladium on carbon, and the like. Examples of the nickel and rhodium catalysts are the above compounds of the palladium catalyst in which palladium is replaced by nickel or rhodium. Specific examples of the copper catalyst are cuprous or cupric halides such as cuprous iodide, cupric iodide, cuprous bromide, cupric bromide, cuprous chloride and cupric chloride, cuprous or cupric oxide, cuprous or cupric cyanide, and the like. They may be used independently or a mixture of two or more catalysts comprising the same metal or different metals. An example of the mixture of the catalysts comprising the different metals is a palladium catalyst-copper catalyst system, in particular, a triphenylphosphine palladium complex-cuprous or -cupric halide system. Among them, the palladium catalysts and the palladium catalyst-copper catalyst system are preferred.

An amount of the metal catalyst are usually from 0.001 to 0.1 equivalent to the tolan derivative [10].

In the above reaction, it may be preferable to use an promoter such as a trivalent phosphorus compound or a trivalent arsenic compound. An example of the promoter is the compound of the above formula [4], in particular, tri-n-butylphosphine, triphenylphosphine, tri-o-tolylphosphine, tri-o-tolylphosphite, phosphorus trichloride, triphenylarsine, and the like.

An amount of the phosphorus or arsenic compound [4] is usually from 0.5 to 50 times equivalents, preferably from 2 to 30 times equivalents to the metal catalyst.

Examples of the base are a carbonate, carboxylic acid salt, alkoxide or hydroxide of an alkali metal, and an organic base such as a primary amine (e.g. butylamine, etc.) and a secondary or tertiary amine (e.g. diethylamine, triethylamine, diisopropylethylamine, tri-n-butylamine, tetramethylethylenediamine, dimethylaniline, morpholine, N-methylmorpholine, pyrrolidine, N-methylpyrrolidine, piperidine, N-methylpiperidine, and the like. Among them, alkali metal hydroxides such as sodium hydroxide and potassium hydroxide, alkali metal carbonates or hydrogencarbonates such as potassium carbonate, sodium carbonate, potassium hydrogencarbonate and sodium hydrogencarbonate, and alkali metal alkoxides such as sodium ethoxide and sodium methoxide are preferred.

An amount of the base is usually from 1 to 5 times equivalent to the tolan derivative [10].

If desired, a solvent may be used. Examples of the solvent are water, methanol, ethanol, isopropanol, tert.-butanol, acetonitrile, tetrahydrofuran, dimethylformamide, hexamethylphosphorylamide, N-methylpyrrolidone, benzene, toluene and the like. An amount of the solvent is not limited.

A reaction temperature in the above reaction is usually from −20° to +190° C., preferably from 20° to 150° C.

After the completion of the reaction, the tolan derivative [10] can be isolated from the reaction mixture by a conventional method such as extraction, distillation, recrystallization, etc. If required, the tolan derivative [10] can be purified by a conventional method such as column chromatography, recrystallization, etc.

Further, the tolan compound [1] of the present invention can be prepared by reacting an ethynyl aromatic compound of the formula [11]:

wherein A, $X^1$, $X^2$, $X^3$ and $X^4$ are the same as defined above with an aromatic derivative of the formula [12]:

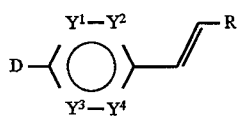 (12)

wherein R, D, Y¹, Y², Y³ and Y⁴ are the same as defined above in the presence of a metal catalyst and a base.

The ethynyl aromatic compound [11] may be synthesized by the following process:

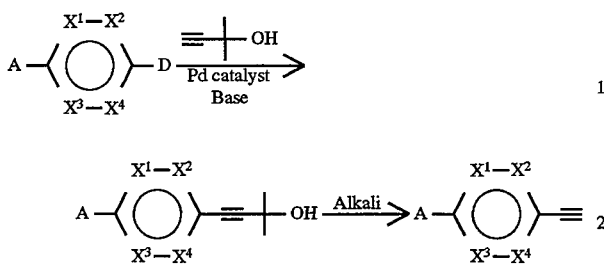

On the other hand, the aromatic derivative [12] may be synthesized by the following process:

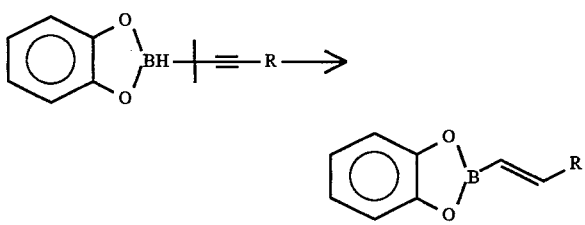

(1) When D is a halogen atom:

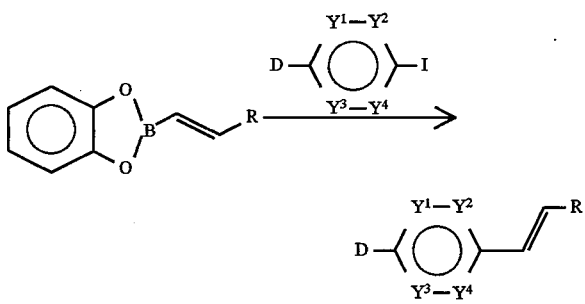

(2) When D is —OSO₂R':

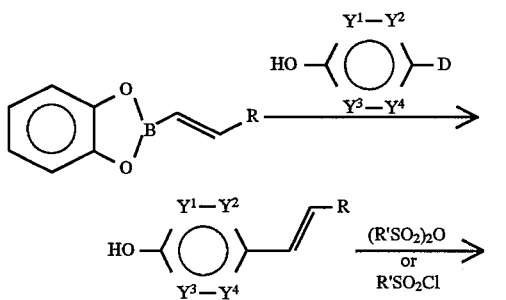

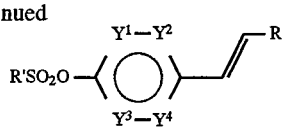

In the reaction for synthesizing the tolan compound [1] from the ethynyl aromatic compound [11] and the aromatic derivative [12], an amount of the ethynyl aromatic compound [11] is usually from 0.9 to 3 times equivalent, preferably from 1 to 2 times equivalent to the aromatic derivative [12]. While it is possible to use an excessive amount of the aromatic derivative [12], it is preferable to use the ethynyl aromatic compound [11] in the excessive amount since the aromatic derivative [12] is generally more expensive than the ethynyl aromatic compound [11].

As the metal catalyst, a palladium catalyst, a nickel catalyst, a rhodium catalyst and a copper catalyst are exemplified. Specific examples of the palladium catalyst are palladium chloride, palladium acetate, triphenylphosphine palladium complex, palladium on carbon, and the like. Examples of the nickel and rhodium catalysts are the above compounds of the palladium catalyst in which palladium is replaced by nickel or rhodium. Specific examples of the copper catalyst are cuprous or cupric halides such as cuprous iodide, cupric iodide, cuprous bromide, cupric bromide, cuprous chloride and cupric chloride, cuprous or cupric oxide, cuprous or cupric cyanide, and the like. They may be used independently or a mixture of two or more catalysts comprising the same metal or different metals. An example of the mixture of the catalysts comprising the different metals is a palladium catalyst-copper catalyst system, in particular, a triphenylphosphine palladium complex-cuprous or-cupric halide system. Among them, the palladium catalysts and the palladium catalyst-copper catalyst system are preferred.

An amount of the metal catalyst are usually from 0.001 to 0.1 equivalent to the aromatic derivative [12].

In the above reaction, it may be preferable to use an promoter such as a trivalent phosphorus compound or a trivalent arsenic compound. An example of the promoter is the compound of the above formula [4], in particular, tri-n-butylphosphine, triphenylphosphine, tri-o-tolylphosphine, tri-o-tolylphosphite, phosphorus trichloride, triphenylarsine, and the like.

An amount of the phosphorus or arsenic compound [4] is usually from 0.5 to 50 times equivalents, preferably from 2 to 30 times equivalents to the metal catalyst.

Examples of the base are a carbonate, carboxylic acid salt, alkoxide or hydroxide of an alkali metal, and an organic base such as a primary amine (e.g. butylamine, etc.) and a secondary or tertiary amine (e.g. diethylamine, triethylamine, diisopropylethylamine, tri-n-butylamine, tetramethylethylenediamine, dimethylaniline, morpholine, N-methylmorpholine, pyrrolidine, N-methylpyrrolidine, piperidine, N-methylpiperidine, and the like. Among them, the secondary and tertiary amines are preferred.

An amount of the base is usually from 1 to 5 times equivalent to the aromatic derivative [12].

If desired, a solvent may be used. Examples of the solvent are toluene, pyridine, picoline, acetonitrile, tetrahydrofuran, dimethylformamide, hexamethylphosphorylamide, N-methylpyrrolidone, methanol, and the like. The above organic base may be used also as a solvent. An amount of the solvent is not limited.

Preferably, the above reaction is carried out in an atmosphere of an inert gas such as nitrogen, argon, and so on.

An yield of the desired compound can be increased by elevating the reaction temperature. But, at a too high temperature, a by-product may be formed. Then, a reaction temperature is preferably from 15° to 160° C., more preferably from 30° to 140° C.

After the completion of the reaction, the tolan compound [1] can be isolated from the reaction mixture by a conventional method such as extraction, distillation, recrystallization, etc. If required, the tolan compound [1] can be purified by a conventional method such as column chromatography, recrystallization, etc.

In the preferred examples of the tolan compound [1] of the present invention, A is methyl, ethyl, propyl, butyl, pentyl, hexyl, heptyl, octyl, nonyl, decyl, undecyl, dodecyl, ethenyl, propenyl, butenyl, pentenyl, hexenyl, heptenyl, octenyl, nonenyl, decenyl, undecenyl, dodecenyl, propynyl, butynyl, pentynyl, hexynyl, heptynyl, octynyl, nonylyl, decynyl, dodecynyl, methoxy, ethoxy, propoxyl, butoxy, pentyloxy, hexyloxy, heptyloxy, octyloxy, nonyloxy, decyloxy, undecyloxy, dodecyloxy, vinyloxy, propenyloxy, butenyloxy, pentenyloxy, hexenyloxy, heptenyloxy, octenyloxy, nonenyloxy, decenyloxy, propynyloxy, butynyloxy, pentynyloxy, hexynyloxy, heptynyloxy, octynyloxy, nonylyloxy, dodecynyloxy, 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, 4-decylcyclohexyl, 4-propylcyclohexenyl, a hydrogen atom, a fluorine atom, trifluoromethyl, trifluoromethoxy, cyano, and the like.

R is preferably methyl, ethyl, propyl, butyl, pentyl, hexyl, heptyl, octyl, nonyl, decyl, undecyl, dodecyl, ethenyl, propenyl, butenyl, pentenyl, hexenyl, heptenyl, octenyl, nonenyl, decenyl, undecenyl, dodecenyl, methoxymethyl, ethoxymethyl, propoxymethyl, butoxymethyl, pentyloxymethyl, hexyloxymethl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropoyl, propoxypropyl, butoxypropyl, pentyloxypropyl, hexyloxypropyl, heptyloxypropyl, octyloxypropyl, nonyloxypropyl, decyloxypropyl, methoxybutyl, ethoxybutyl, propoxybutyl, butoxybutyl, pentyloxybutyl, hexyloxybutyl, heptyloxybutyl, octyloxybutyl, nonyloxybutyl, decyloxybutyl, methoxypentyl, ethoxypentyl, propoxypentyl, butoxypentyl, pentyloxypentyl, hexyloxypentyl, heptyloxypentyl, octyloxypentyl, and so on.

Preferred examples of the ring comprising the $X^1$ to $X^4$ or Y to $Y^4$ are 2,5-substituted pyridine ring, 2,5-substituted pyrimidine ring, 2,5-substituted pyrazine ring, 3,6-substituted pyridazine ring, 3,6-substituted triazine ring, 3,6-substituted tetrazine ring, and so on.

The tolan compound [1] can be used as a component of a liquid crystal composition. In such case, the tolan compound [1] is contained in an amount of 0.1 to 99.9% by weight, preferably 1 to 99% by weight of the whole weight of the liquid crystal composition.

As other component constituting the liquid crystal composition, any of conventionally used liquid crystals may be used.

Examples of such other component are

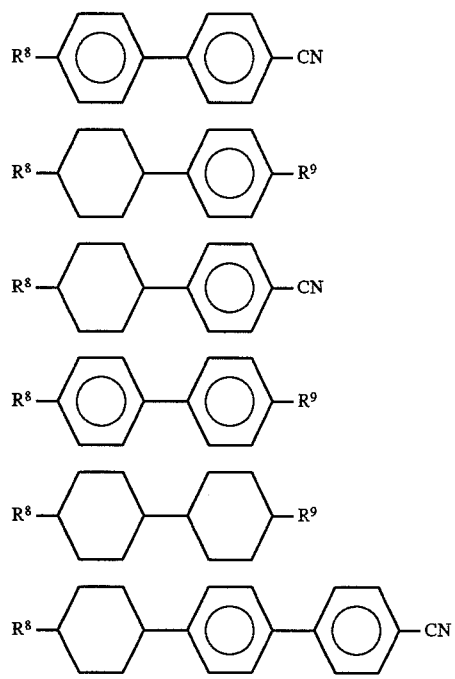

($R^8$: alkyl or alkoxy group, $R^9$: alkyl or alkoxy group)

Such liquid crystal composition can be used in the same way as the conventional liquid crystal compositions, in particular, in a liquid crystal element such as an optical switching element. A structure of the liquid crystal element may be the same as that of the conventional liquid crystal element.

The tolan compound [1] has a larger anisotropy of refractive index than the conventional liquid crystal materials.

Even when the tolan compound [1] itself does not have any liquid crystal phase, the addition of such tolan compound [1] to the liquid crystal composition increases the anisotropy of refractive index of the liquid crystal composition without increasing a viscosity of the composition. In view of the liquid crystal property, the carbon number of R or $R^1$ is preferably at least 2.

For example, to achieve the high response speed of a STN liquid crystal element for which demand is increasing recently, it is required to decrease a cell width. The tolan compound [1] of the present invention is useful as a component of such liquid crystal composition or element, since it has the large anisotropy of refractive index and the low viscosity.

PREFERRED EMBODIMENT OF THE INVENTION

The present invention will be illustrated by the following examples, which are only for explanation purpose and do not limit the scope of the present invention.

Measurement of an optical anisotropy value of a tolan compound

Optical anisotropy value: Δn

An optical anisotropy value of a tolan compound [1] was obtained by extrapolation from an optical anisotropy value of a liquid crystal composition comprising 85% by weight of the following matrix liquid crystal mixture and 15% by weight of the tolan compound and that of the matrix liquid crystal mixture at 25° C. using a light having a wavelength of 550 nm.

| Matrix liquid crystal mixture | |
|---|---|
| Compound | Wt. % |
| $C_3H_7$–(cyclohexyl)–(phenyl)–CN | 24 |
| $C_5H_{11}$–(cyclohexyl)–(phenyl)–CN | 36 |
| $C_7H_{15}$–(cyclohexyl)–(phenyl)–CN | 25 |
| $C_5H_{11}$–(cyclohexyl)–(phenyl)–(phenyl)–CN | 15 |

The optical anisotropy value of the tolan compound [1] is calculated according to the following equation:

$$\Delta n \text{ of the tolan compound} = \frac{1}{3} \times (20b - 17a)$$

wherein a is an optical anisotropy value of the matrix liquid crystal mixture and b is an optical anisotropy value of the liquid crystal composition comprising 85% by weight of the matrix liquid crystal mixture and 15% by weight of the tolan compound [1].

Reference Example 1

In a four necked flask equipped with a stirrer and a thermometer which had been replaced by a nitrogen atmosphere, 1-n-pentyne (13.6 g, 200 mmol) was charged, and then catecholborane (12 g, 100 mmol) was dropwise added. After mixing them at room temperature for 1 hour, they were reacted at 70° C. for 2 hours. After cooling the flask to room temperature, unreacted 1-n-pentyne was evaporated off under reduced pressure to obtain E-1-pentenyl-catecholborane.

Reference Example 2

In a four necked flask equipped with a stirrer and a thermometer which had been replaced by a nitrogen atmosphere, 3-ethoxy-1-propyne (8.4 g, 100 mmol) was charged, and then catecholborane (6 g, 50 mmol) was dropwise added. After mixing them at room temperature for 1 hour, they were reacted at 70° C. for 2 hours. After cooling the flask to room temperature, unreacted 3-ethoxy-1-propyne was evaporated off under reduced pressure to obtain E-1-(3-ethoxy)propenylcatecholborane.

In the same manner as above, various boron compounds [6] are prepared.

Reference Example 3

In a four necked flask equipped with a stirrer and a thermometer which had been replaced by a nitrogen atmosphere, 4-iodo-1-boromobenzene (100 g, 0.35 mol), bis(triphenylphosphine)palladium chloride (0.5 g), cuprous iodide (0.5 g), triphenylphosphine (1 g), triethylamine (80 g) and toluene (300 g) were charged. Then, to the mixture, 1,1-dimethyl-2-propyn-1-ol (32.7 g, 0.39 mol) was dropwise added at 80° C. over 2 hours, followed by stirring at the same temperature for 5 hours. After cooling the reaction mixture to room temperature, hydrochloric acid was added to the mixture to make its pH neutral. Then, an organic layer was separated and washed with water. The organic layer was concentrated and purified by chromatography to obtain 4-(3-hydroxy-3,3-dimethyl-1-propynyl)-1-bromobenzene (72 g). Yield: 85%. Melting point: 62° C.

$^1$H-NMR (CDCl$_3$): δ (ppm)=1.6 (s, 6H), 1.75 (s, 1H), 7.25–7.45 (m, 4H).

According to the procedure of Reference Example 3, various carbinol compounds [5] are prepared.

EXAMPLE 1

(1) In a four necked flask equipped with a stirrer, a reflux condenser and a thermometer which had been replaced by a nitrogen atmosphere, 4-(3-hydroxy-3,3-dimethyl-1-propynyl)-1-bromobenzene (3.6 g, 15 mmol), tetrakis(triphenylphosphine)palladium (0.06 g, 0.05 mmol), sodium hydroxide (0.8 g, 20 mmol) and tetrahydrofuran (60 ml) were charged. Then, to the mixture, a solution of E-1-pentenylcatecholborane prepared in Reference Example 1 (20 mmol) in tetrahydrofuran (50 ml) was dropwise added at room temperature, followed by heat refluxing for 6 hours while stirring. After cooling the reaction mixture to room temperature, 30% aqueous hydrogen peroxide (2 ml) was added to the mixture, followed by stirring for 1 hour. The mixture was extracted with toluene and water. The organic layer was washed with water twice and dried over anhydrous magnesium sulfate. After removing the solvents, the residue was purified by silica gel column chromatography to obtain 4-(3-hydroxy-3,3-dimethyl-1-propynyl)-1-(1-trans-pentenyl)benzene (2.8 g). Yield: 83%. Melting point: 65° C.

Elementary analysis ($C_{16}H_{20}O$): Calculated: C, 84.16; H, 8.83 Found: C, 84.03; H, 8.73

$^1$H-NMR (CDCl$_3$): δ (ppm)=0.95 (t, 3H), 1.5 (m, 2H), 1.60 (s, 6H), 2.1 (s, 1H), 2.2 (m, 2H), 6.2–6.4 (m, 2H), 7.2–7.4 (m, 4H).

(2) Then, a mixture of obtained 4-(3-hydroxy-3,3-dimethyl-1-propynyl)-1-(1-trans-pentenyl)benzene (2.3 g, 10 mmol), sodium hydroxide (0.8 g, 20 mmol) and toluene (25 ml) was refluxed for 2 hours while stirring, during which the solvent was evaporated off.

After the completion of the reaction, the reaction mixture was cooled to room temperature. After adding water (10 ml), the mixture was phase separated, and the organic layer was washed with water twice and dried over anhydrous magnesium sulfate. After evaporation the solvent off, the residue was purified by silica gel column chromatography to obtain 4-(1-trans-pentenyl)phenylacetylene (1.6 g). Yield: 96%.

$n_D^{20}$: 1.5729.

Elementary analysis ($C_{13}H_{14}$): Calculated: C, 91.71; H, 8.29 Found: C, 91.52; H, 8.23

$^1$H-NMR (CDCl$_3$): δ (ppm)=0.95 (t, 3H), 1.5 (m, 2H), 2.2 (m, 2H), 3.1 (s, 1H), 6.2–6.4 (m, 2H), 7.2–7.5 (m, 4H).

EXAMPLE 2

(2) In a four necked flask equipped with a stirrer, a reflux condenser and a thermometer which had been replaced by a nitrogen atmosphere, 4-(3-hydroxy-3,3-dimethyl-1-propynyl)-3-fluoro-1-bromobenzene (3.9 g, 15 mmol), bis(triphenylphosphine)palladium chloride (0.07 g, 0.1 mmol), sodium hydroxide (1.2 g, 30 mmol), tetrahydrofuran (40 ml) and N-methylpyrrolidone (5 ml) were charged. Then, to the mixture, a solution of E-1-pentenylcatecholborane prepared in Reference Example 1 (20 mmol) in tetrahydrofuran (50 ml) was dropwise added at room temperature, followed by heat refluxing for 6 hours while stirring. After cooling the reaction mixture to room temperature, 30% aqueous hydrogen peroxide (2 ml) was added to the mixture, followed by stirring for 1 hour. The mixture was extracted with toluene and water. The organic layer was washed with water twice and dried over anhydrous magnesium sulfate. After evaporating the solvent off, the residue was purified by silica gel column chromatography to obtain 4-(3-hydroxy-3,3-dimethyl-1-propynyl)-1-(1-trans-pentenyl)-3-fluorobenzene (3.1 g). Yield: 84%. Melting point: 62° C.

Elementary analysis ($C_{16}H_{19}FO$): Calculated: C, 78.02; H, 7.77 Found: C, 78.09; H, 7.66

(2) Then, a mixture of obtained 4-(3-hydroxy-3,3-dimethyl-1-propynyl)-1-(1-trans-pentenyl)-3-fluorobenzene (2.5 g, 10 mmol), potassium hydroxide (0.9 g, 15 mmol) and toluene (25 ml) was refluxed for 1 hour while stirring, during which the solvent was evaporated off.

After the completion of the reaction, the reaction mixture was cooled to room temperature. After adding water (10 ml), the mixture was phase separated, and the organic layer was washed with water twice and dried over anhydrous magnesium sulfate. After evaporating the solvent off, the residue was purified by silica gel column chromatography to obtain [4-(1-trans-pentenyl)-2-fluorophenyl]acetylene (1.8 g). Yield: 96%.

$n_D^{20}$:1.5619. Elementary analysis ($C_{13}H_{13}F$): Calculated: C, 82.95; H, 6.96

Found: C, 83.06; H, 6.79

EXAMPLE 3

In the same manner as in the first step of Example 2 except that a solution of E-1-heptenylcatecholborane (20 mmol) in tetrahydrofuran (50 ml) was used in place of the solution of E-1-pentenylcatecholborane and 4-(3-hydroxy-3,3-dimethyl-1-propynyl)-2-fluoro-1-bromobenzene (3.9 g, 15 mmol) was used in place of 4-(3-hydroxy-3,3-dimethyl-1-propynyl)-3-fluoro-1-bromobenzene, the reaction was carried out to obtain 4-(3-hydroxy-3,3-dimethyl-1-propynyl)-1-(1-trans-heptenyl)-2-fluorobenzene (3.3 g). Yield: 81%.

Elementary analysis ($C_{18}H_{23}FO$): Calculated: C, 78.79; H, 8.45 Found: C, 78.85; H, 8.32

Further, in the same manner as in the second step of Example 2 except that 4-(3-hydroxy-3,3-dimethyl-1-propynyl)-1-(1-trans-heptenyl)-2-fluorobenzene was used in place of 4-(3-hydroxy-3,3-dimethyl-1-propynyl)-1-(1-trans-pentenyl)-3-fluorobenzene, the reaction was carried out to obtain [4-(1-trans-heptenyl)-3-fluorophenyl]acetylene (2.0 g). Yield: 94%.

$n_D^{20}$1.5494.

Elementary analysis ($C_{15}H_{17}F$): Calculated: C, 83.29; H, 7.92 Found: C, 83.21; H, 7.81

EXAMPLE 4

In the same manner as in the first step of Example 1 except that a solution of E-1-butenylcatecholborane (20 mmol) in tetrahydrofuran (50 ml) was used in place of the solution of E-1-pentenylcatecholborane, the reaction was carried out to obtain 4-(3-hydroxy- 3,3-dimethyl-1-propynyl)-1-(1-trans-butenyl)benzene (3.3 g). Yield: 84%.

Elementary analysis ($C_{15}H_{18}O$): Calculated: C, 84.07; H, 8.47 Found: C, 83.93; H, 8.61

Further, in the same manner as in the second step of Example 1 except that 4-(3-hydroxy-3,3-dimethyl-1-propynyl)-1-(1-trans-butenyl)benzene was used, the reaction was carried out to obtain [4-(1-trans-butenyl)phenyl]acetylene (1.5 g). Yield: 96%.

$n_D^{20}$: 157894.

Elementary analysis ($C_{12}H_{12}$): Calculated: C, 92.26; H, 7.74 Found: C, 92.11; H, 7.84

EXAMPLE 5

In a four necked flask equipped with a stirrer, a reflux condenser and a thermometer which had been replaced by a nitrogen atmosphere, 4-(3-hydroxy-3,3-dimethyl-1-propynyl)-1- trifluoromethanesulfonyloxybenzene (3.6 g, 15 mmol), tetrakis(triphenylphosphine)palladium (0.06 g, 0.05 mmol), sodium hydroxide (1.2 g, 30 mmol) and tetrahydrofuran (60 ml) were charged. Then, to the mixture, a solution of E-1-pentenylcatecholborane prepared in Reference Example 1 (20 mmol) in tetrahydrofuran (50 ml) was dropwise added at room temperature, followed by heat refluxing for 6 hours while stirring. After cooling the reaction mixture to room temperature, 30% aqueous hydrogen peroxide (2 ml) was added to the mixture, followed by stirring for 1 hour. The mixture was extracted with toluene and water. The organic layer was washed with water twice and dried over anhydrous magnesium sulfate. After evaporating the solvent off, the residue was purified by silica gel column chromatography to obtain 4-(3-hydroxy-3,3-dimethyl-1-propynyl)-1-(1-trans-pentenyl)benzene (2.8 g). Yield: 82%.

Then, a mixture of obtained 4-(3-hydroxy-3,3-dimethyl-1-propynyl)-1-(1-trans-pentenyl)benzene (2.3 g, 10 mmol), potassium hydroxide (1.1 g, 20 mmol) and toluene (25 ml) was refluxed for 2 hours while stirring, during which the solvent was evaporated off.

After the completion of the reaction, the reaction mixture was cooled to room temperature. After adding water (10 ml), the mixture was phase separated, and the organic layer was washed with water twice and dried over anhydrous magnesium sulfate. After evaporating the solvent off, the residue was purified by silica gel column chromatography to obtain 4-(1-trans-pentenyl)phenylacetylene (1.6 g). Yield: 95%.

EXAMPLE 6

In a four necked flask equipped with a thermometer and a stirrer, 4-propyl-1-bromobenzene (5.2 g, 0.026 mol), 4-(1-trans-phentenyl)phenylacetylene (3.4 g, 0.02 mol), bis (triphenylphosphine)palladium chloride (0.13 g), cuprous iodide (0.15 g), triphenylphosphine (0.8 g) and triethylamine (40 ml) were charged and refluxed under nitrogen atmosphere for 6 hours.

After the completion of the reaction, the reaction mixture was poured in water (100 ml) and extracted with toluene (100 ml). The toluene layer was washed with 3% hydrochloric acid and then water, followed by concentration under reduced pressure to obtain a pale yellow residue. Then, the residue was purified by silica gel column chromatography (eluent: toluene-hexane) to obtain 1-(4-propylphenyl)- 2-[4-(1-trans-pentenyl)phenyl]acetylene (4.5 g). Yield: 77%.

Optical anisotropy value Δn of 1-(4-propylphenyl)-2-[4-(1-trans-pentenyl)phenyl]acetylene: 0.343.

EXAMPLE 7

In a four necked flask equipped with a thermometer and a stirrer, 4-cyano-1-trifluoromethanesulfonyloxybenzene (6.4 g, 0.026 mol), 4-(1-trans-pentenyl)phenylacetylene (3.4 g, 0.02 mol), bis(triphenylphosphine)palladium chloride (0.15 g), cuprous iodide (0.15 g), triphenylphosphine (0.6 g), triethylamine (20 ml) and N-methylpiperazine (30 ml) were charged and refluxed under nitrogen atmosphere for 6 hours.

After the completion of the reaction, the reaction mixture was poured in water (100 ml) and extracted with toluene (100 ml). The toluene layer was washed with 3% hydrochloric acid and then water, followed by concentration under reduced pressure to obtain a pale yellow residue. Then, the residue was purified by silica gel column chromatography (eluent: toluene-hexane) to obtain 1-(4-cyanophenyl)-2-[4-(1-trans-pentenyl)phenyl]acetylene (4.5 g). Yield: 83%.

Optical anisotropy value Δn of 1-(4-cyanophenyl)-2-[4-(1-trans-pentenyl)phenyl]acetylene: 0.523.

EXAMPLE 8

In a four necked flask equipped with a thermometer and a stirrer, 4-cyano-3-fluoro-1-bromobenzene (4.6 g, 0.022 mol), bis(triphenylphosphine)palladium chloride (0.12 g), cuprous iodide (0.15 g), triphenylphosphine (0.8 g) and triethylamine (40 ml) were charged and refluxed under nitrogen atmosphere for 6 hours.

After the completion of the reaction, the reaction mixture was poured in water (100 ml) and extracted with toluene (100 ml). The toluene layer was washed with 3% hydrochloric acid and then water, followed by concentration under reduced pressure to obtain a residue. Then, the residue was purified by silica gel column chromatography (eluent:toluene-hexane) to obtain 1-(4-cyano-3-fluorophenyl)-2-[4-(1-trans-pentenyl)phenyl]acetylene (4.4 g). Yield: 76%.

Optical anisotropy value Δn of 1-(4-cyano-3-fluorophenyl)-2-[4-(1-trans-pentenyl)phenyl]acetylene: 0.403.

EXAMPLE 9

In a four necked flask equipped with a thermometer and a stirrer, 4-fluoro-1-methanesulfonyloxybenzene (6.3 g, 0.026 mol), 4-(1-trans-pentenyl)phenylacetylene (3.4 g, 0.02 mol), bis(triphenylphosphine chloride (0.15 g), cuprous iodide (0.2 g), triphenylphosphine (0.5 g), methylmorpholine (20 ml) and N-methylpyrrolidone (30 ml) were charged and refluxed under nitrogen atmosphere for 15 hours.

After the completion of the reaction, the reaction mixture was concentrated under reduced pressure. To the residue, 3% hydrochloric acid and ethyl acetate (60 ml) were added. The organic layer was washed with water and concentrated under reduced pressure. The residue was purified by silica gel column chromatography (eluent:ethyl acetate-hexane) to obtain 1-(4-fluorophenyl)-2-[4-(1-trans-pentenyl)phenyl]acetylene (4.3 g). Yield: 81%.

Optical anisotropy value Δn of 1-(4-fluorophenyl)-2-[4-(1-trans-pentenyl)phenyl]acetylene: 0.323.

EXAMPLE 10

In the same manner as in Example 9 except that 3,4,5-trifluoro-1-bromobenzene (5.3 g, 0.025 mol) was used in place of 4-fluoro-1-methanesulfonyloxybenzene, the reaction was carried out to obtain 1-(3,4,5-trifluorophenyl)-2-[4-(1-trans-pentenyl)phenyl]acetylene (4.5 g). Yield: 75%.

EXAMPLE 11

In a four necked flask equipped with a thermometer and a stirrer, 4-(4-propylcyclohexyl)-1-bromobenzene (4.2 g, 0.015 mol), 4-(1-trans-pentenyl)phenylacetylene (1.7 g, 0.01 mol), bis(triphenylphosphine)palladium chloride (0.07 g), cuprous iodide (0.09 g), triphenylphosphine (0.15 g) and triethylamine (30 ml) were charged and reacted at 80° C. for 10 hours under nitrogen atmosphere.

After the completion of the reaction, the reaction mixture was concentrated under reduced pressure. To the residue, 3% hydrochloric acid and ethyl acetate (60 ml) were added. The organic layer was washed with water and concentrated under reduced pressure. The residue was purified by silica gel column chromatography (eluent:ethyl acetate-hexane) to obtain 1-(4-propylcyclohexyl)phenyl-2-[4-(1-trans-pentenyl)phenyl]acetylene (2.8 g). Yield: 76%.

Optical anisotropy value Δn of 1-(4-propylcyclohexyl)phenyl-2-[4-(1-trans-pentenyl)phenyl]acetylene: 0.356.

EXAMPLE 12

In the same manner as in Example 11 except that 2-fluoro-4-(1-trans-pentenyl)phenylacetylene (1.9 g, 0.01 mol) was used in place of 4-(1-trans-pentenyl)phenylacetylene, the reaction was carried out to obtain 1-(4-propylcyclohexyl)phenyl-2-[2-fluoro-4-(1-trans-pentenyl)phenyl]acetylene (2.9 g). Yield: 75%.

EXAMPLE 13

In a four necked flask equipped with a thermometer and a stirrer, 4-octyloxybromobenzene (3.4 g, 0.012 mol), 5-(1-trans-nonenyl)-2-ethynylpyrimidine (2.3 g, 0.01 mol), bis(triphenylphosphine)palladium chloride (0.15 g), cuprous iodide (0.15 g), triphenylphosphine (0.15 g) and triethylamine (30 ml) were charged and reacted at a temperature of 80° to 85° C. for 6 hours.

After the completion of the reaction, the reaction mixture was concentrated under reduced pressure. To the residue, toluene (60 ml) and water were added. The toluene layer was washed with water and concentrated. The residue was purified by silica gel column chromatography (eluent:toluene) to obtain 1-(4-octyloxyphenyl)-2-[5-(1-trans-nonenyl)pyrimidin-2-yl]acetylene (3.1 g). Yield: 71%.

EXAMPLE 14

In the same manner as in Example 6 except that 4-propyl-2-fluoro-1-bromobenzene (5.6 g, 0.026 mol) was used in place of 4-propyl-1-bromobenzene, the reaction was carried out to obtain 1-(4-propyl-2-fluorophenyl)-2-[4-(1-trans-pentenyl)phenyl]acetylene (4.4 g). Yield: 72%.

Phase sequence of 1-(4-propyl-2-fluorophenyl)-2-[4-(1-trans-pentenyl)phenyl]acetylene: K-35-N-70-I (K: Crystal phase, N: Nematic Phase, I: Isotropic liquid phase).

EXAMPLE 15

In a four necked flask equipped with a thermometer and a stirrer, 4-cyano-3-fluorophenylacetylene (3.2 g, 0.022 mol), 4-(1-trans-pentenyl)-bromobenzene (4.4 g, 0.02 mol), bis(triphenylphosphine)palladium chloride (0.13 g), cuprous iodide (0.13 g), triphenylphosphine (0.7 g) and triethylamine (40 ml) were charged and refluxed for 6 hours under nitrogen atmosphere.

After the completion of the reaction, the reaction mixture was poured in water (100 ml) and extracted by toluene (100 ml).

The toluene layer was washed with 3% hydrochloric acid and then water and concentrated under reduced pressure. The residue was purified by silica gel column chromatography (eluent:toluene-hexane) to obtain 1-(4-cyano-3-fluorophenyl)-2-[4-(1-trans-pentenyl)phenyl]acetylene (4.3 g). Yield: 75%.

EXAMPLE 16

In a four necked flask equipped with a thermometer and a stirrer, 3,4-difluorophenylacetylene (3.5 g, 0.025 mol), 4-(1-trans-pentenyl)-bromobenzene (4.5 g, 0.02 mol), bis(triphenylphosphine)palladium chloride (0.15 g), cuprous iodide (0.2 g), triphenylphosphine (0.25 g), methylmorpholine (20 ml) and N-methylpyrrolidone (30 ml) were charged and refluxed for 15 hours under nitrogen atmosphere.

After the completion of the reaction, the reaction mixture was concentrated under reduced pressure. To the residue, 3% hydrochloric acid and ethyl acetate (60 ml) were added, and the organic layer was washed with water and concentrated under reduced pressure. The residue was purified by silica gel column chromatography (eluent:ethyl acetate-hexane) to obtain 1-(3,4-difluorophenyl)-2-[4-(1-trans-pentenyl)phenyl]acetylene (4.3 g). Yield: 76%.

Optical anisotropy value $\Delta n$ of 1-(3,4-difluorophenyl)-2-[4-(1-trans-pentenyl)phenyl]acetylene: 0.249.

EXAMPLE 17

In a four necked flask equipped with a thermometer and a stirrer, 4-(4-propylcyclohexyl)phenylacetylene (3.4 g, 0.015 moll, 4-(1-trans-pentenyl)-bromobenzene (2.3 g, 0.01 mol), bis(triphenylphosphine)palladium chloride (0.06 g), cuprous iodide (0.06 g), triphenylphosphine (0.15 g) and triethylamine (30 ml) were charged and refluxed at 80° C. for 10 hours under nitrogen atmosphere.

After the completion of the reaction, the reaction mixture was concentrated under reduced pressure. To the residue, 3% hydrochloric acid and ethyl acetate (60 ml) were added, and the organic layer was washed with water and concentrated under reduced pressure. The residue was purified by silica gel column chromatography (eluent:ethyl acetate-hexane) to obtain 1-(4-propylcyclohexyl)phenyl-2-[4-(1-trans-pentenyl)phenyl]acetylene (2.8 g). Yield: 75%.

EXAMPLE 18

In the same manner as in Example 17 except that 4-(4-propylcyclohexenyl)phenylacetylene, (3.4 g, 0.015 moll was used in place of 4-(4-propylcyclohexyl)phenylacetylene, the reaction was carried out to obtain 1-(4-propylcyclohexenyl)phenyl-2-[4-(1-trans-pentenyl)phenyl]acetylene (2.7 g). Yield: 72%.

Phase sequence of 1-(4-propylcyclohexenyl)phenyl-2-[4-(1-trans-pentenyl)phenyl]acetylene: K-125-Sx-152-N-247-I (K: Crystalline phase, Sx: Smectic phase without identification of molecular arrangement, N: Nematic phase, I: Isotropic liquid phase).

EXAMPLE 19

In a four necked flask equipped with a thermometer and a stirrer, 4-trifluoromethylphenylacetylene (4.3 g, 0.025 mol), 4-(1-trans-pentenyl)bromobenzene (4.5 g, 0.02 mol), bis(triphenylphosphine)palladium chloride (0.15 g), cuprous iodide (0.2 g), triphenylphosphine (0.25 g), methylmorpholine (20 ml) and N-methylpyrrolidone (30 ml) were charged and refluxed for 15 hours under nitrogen atmosphere.

After the completion of the reaction, the reaction mixture was concentrated under reduced pressure. To the residue, 3% hydrochloric acid and ethyl acetate (60 ml) were added, and the organic layer was washed with water and concentrated under reduced pressure. The residue was purified by silica gel column chromatography (eluent:ethyl acetate-hexane) to obtain 1-(4-trifluoromethylphenyl)-2-[4-(1-trans-pentenyl)phenyl]acetylene (4.7 g). Yield: 75%.

EXAMPLE 20

In a four necked flask equipped with a thermometer and a stirrer, 4-octyloxyphenylacetylene (2.8 g, 0.012 mol), 4-(1-trans-nonenyl)-1-bromobenzene (2.8 g, 0.01 mol), bis(triphenylphosphine)palladium chloride (0.1 g), cuprous iodide (0.1 g), triphenylphosphine (0.15 g) and triethylamine (40 ml) were charged and reacted at a temperature of 80° to 85° C. for 6 hours.

After the completion of the reaction, the reaction mixture was concentrated under reduced pressure. To the residue, toluene and water were added, and the toluene layer was washed with water and concentrated under reduced pressure. The residue was purified by chromatography to obtain 1-(4-octyloxyphenyl)-2-[4-(1-trans-nonenyl)phenyl]acetylene (3.2 g). Yield: 74%.

EXAMPLE 21

In a four necked flask equipped with a stirrer, a reflux condenser and a thermometer which had been replaced by a nitrogen atmosphere, 1-(4-propylphenyl)-2-(4-trifluoromethanesulfonyloxyphenyl)acetylene (4.4 g, 12 mmol), tetrakis(triphenylphosphine)palladium (0.23 g, 0.2 mmol), sodium hydroxide (2.4 g, 60 mmol), tetrahydrofuran (40 ml) and N-methylpiperazine (10 ml) were charged. Then, to the mixture, a solution of E-1-pentenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After evaporating the solvent off, the residue was purified by silica gel column chromatography to obtain 1-(4-propylphenyl)-2-[4-(1-trans-pentenyl)phenyl]acetylene (3.0 g). Yield: 88%.

EXAMPLE 22

In a four necked flask equipped with a stirrer, a reflux condenser and a thermometer which had been replaced by a nitrogen atmosphere, 1-(4-cyanophenyl)-2-(4-bromophenyl)acetylene (3.4 g, 12 mmol), tetrakis(triphenylphosphine)palladium (0.23 g, 0.2 mmol), N-methylpiperidine (5 g), potassium carbonate (5.5 g, 40 mmol) and tetrahydrofuran (60 ml) were charged. Then, to the mixture, a solution of E-1-pentenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After evaporating the solvent off, the residue was purified by silica gel column chromatography to obtain 1-(4-cyanophenyl)-2-[4-(1-trans-pentenyl)phenyl]acetylene (2.7 g). Yield: 84%.

EXAMPLE 23

In the same manner as in Example 22 except that 1-(4-cyano-3-fluorophenyl)-2-(2-fluoro-4-bromophenyl)acetylene (3.8 g, 12 mmol) was used in place of 1-(4-cyanophenyl)-2-(4-bromophenyl)acetylene, the reaction was carried out to obtain 1-(4-cyano-3-fluorophenyl)-2-[2-fluoro-4-(1-trans-pentenyl)phenyl]acetylene (3.1 g). Yield: 83%.

EXAMPLE 24

In a four necked flask equipped with a stirrer, a reflux condenser and a thermometer which had been replaced by a nitrogen atmosphere, 1-(4-fluorophenyl)-2-(4-bromophenyl)acetylene (3.3 g, 12 mmol), tetrakis(triphenylphosphine)palladium (0.23 g, 0.2 mmol), sodium hydroxide (2.4 g, 60 mmol) and tetrahydrofuran (60 ml) were charged. Then, to the mixture, a solution of E-1-pentenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After evaporating the solvent off, the residue was purified by silica gel column chromatography to obtain 1-(4-fluorophenyl)-2-[4-(1-trans-pentenyl)phenyl]acetylene (2.7 g). Yield: 84%.

EXAMPLE 25

In a four necked flask equipped with a stirrer, a reflux condenser and a thermometer which had been replaced by a nitrogen atmosphere, 1-[4-(1-pentenyl)phenyl]-2-(4-bromophenyl)acetylene (3.9 g, 12 mmol), tetrakis(triphenylphosphine)palladium (0.23 g, 0.2 mmol), sodium hydroxide (2.4 g, 60 mmol) and tetrahydrofuran (60 ml) were charged. Then, to the mixture, a solution of E-1-pentenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After evaporating the solvent off, the residue was purified by silica gel column chromatography to obtain 1-[4-(1-pentenyl)phenyl]-2-[4-(1-trans-pentenyl)phenyl]acetylene (3.2 g). Yield: 84%.

Phase sequence of 1-[4-(1-pentenyl)phenyl]-2-[4-(1-trans-pentenyl)phenyl]acetylene: K-131-N-165-I (K: Crystalline phase, N: Nematic phase, I: Isotropic liquid phase).

EXAMPLE 26

In the same manner as in Example 25 except that 1-[4-(1-pentynyl)phenyl]-2-(4-bromophenyl)acetylene (3.9 g, 12 mmol) was used in place of 1-[4-(1-pentenyl)phenyl]-2-(4-bromophenyl)acetylene, the reaction was carried out to obtain 1-[4-(1-pentynyl)phenyl]-2-[4-(1-trans-pentenyl)phenyl]acetylene (3.1 g). Yield: 82%.

EXAMPLE 27

In the same manner as in Example 25 except that 1-(2-fluoro-4-methylphenyl)-2-(4-bromophenyl)acetylene (3.5 g, 12 mmol) was used in place of 1-[4-(1-pentenyl)phenyl]-2-(4-bromophenyl)acetylene, the reaction was carried out to obtain 1-(2-fluoro-4-methylphenyl)-2-[4-(1-trans-pentenyl)phenyl]acetylene (2.9 g). Yield: 86%.

EXAMPLE 28

In a four necked flask equipped with a thermometer and a stirrer, 1-(4-octyloxyphenyl)-2-(4-bromo-3-fluorophenyl)acetylene (4.8 g, 0.012 mol), tetrakis(triphenylphosphine)palladium (0.23 g, 0.2 mmol), toluene (50 ml), sodium carbonate (10.6 g, 0.1 mol) and water (90 ml) were charged. Then, to the mixture, E-1-nonenyl-dihydroxyborane (2.5 g, 0.015 mol) was added and reacted at a temperature of 80° to 85° C. for 6 hours. After cooling the reaction mixture, the aqueous layer was separated off, and the organic layer was washed with water. The organic layer was concentrated under reduced pressure, and the residue was purified by silica gel column chromatography to obtain 1-(4-octyloxyphenyl)-2-[4-(1-trans-nonenyl)-3-fluorophenyl]acetylene (3.9 g). Yield: 73%.

EXAMPLE 29

In a four necked flask equipped with a stirrer, a reflux condenser and a thermometer which had been replaced by a nitrogen atmosphere, 1-[4-(4-propylcyclohexyl)phenyl]-2-(2-fluoro-4-bromophenyl)acetylene (4.8 g, 12 mmol), tetrakis(triphenylphosphine)palladium (0.23 g, 0.2 mmol), sodium hydroxide (2.4 g, 60 mmol) and tetrahydrofuran (60 ml) were charged. Then, to the mixture, a solution of E-1-pentenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After evaporating the solvent off, the residue was purified by silica gel column chromatography to obtain 1-[4-(4-propylcyclohexyl)phenyl]-2-[2-fluoro-4-(1-trans-pentenyl)phenyl]acetylene (3.8 g). Yield: 81%.

EXAMPLE 30

In a four necked flask equipped with a stirrer, a reflux condenser and a thermometer which had been replaced by a nitrogen atmosphere, 1-(4-trifluoromethylphenyl)-2-(4-bromophenyl)acetylene (3.9 g, 12 mmol), tetrakis(triphenylphosphine)palladium (0.23 g, 0.2 mmol), sodium hydroxide (2.4 g, 60 mmol) and tetrahydrofuran (60 ml) were charged. Then, to the mixture, a solution of E-1-heptenylcatecholborane (20 mmol) in tetrahydrofuran (50 ml) was dropwise added at room temperature, followed by heat refluxing for 6 hours while stirring. After cooling the reaction mixture to room temperature, 10% aqueous solution of sodium hydroxide (5 ml) and 30% aqueous hydrogen peroxide (2 ml) were added to the mixture, followed by stirring for 1 hour. The mixture was extracted with ethyl ether. The organic layer was washed with saturated aqueous solution of sodium chloride (20 ml each) twice and dried over anhydrous magnesium sulfate. After removing the solvent, the residue was purified by silica gel column chromatography to obtain 1-(4-trifluoromethylphenyl)-2-[4-(1-trans-pentenyl)phenyl]acetylene (3.2 g). Yield: 84%.

By carrying out the reactions in the analogous way to those of Examples 6–30, the following tolan compounds [1] are obtained:

1-(4-trifluoromethoxyphenyl)-2-[4-(1-trans-pentenyl)-3-fluorophenyl]acetylene,

1-[4-(1-pentynyl)-3-fluorophenyl]-2-[4-(3-ethoxy-1-trans-propenyl)phenyl]acetylene, 1-(4-decyloxy-2,3-difluorophenyl)-2-[4-(1-trans-heptenyl)-3-fluorophenyl]acetylene, 1-[4-(2-butenyloxy)-3-fluorophenyl]-2-[4-(1-trans-butenyl)phenyl]acetylene, 1-[4-(4-propylcyclohexyl)phenyl]-2-[4-(1-trans-propenyl)-3-fluorophenyl]acetylene, 1-[4-(4-propyl-1-cyclohexenyl)phenyl]-2-[4-(1-trans-pentenyl)phenyl]acetylene, 1-[4-(4-propylcyclohexyl)phenyl]-2-[4-(1-trans-pentenyl)phenyl]acetylene, 1-(4-fluorophenyl)-2-[4-(1-trans-pentenyl)-2-fluorophenyl]acetylene, 1-phenyl-2-[4-(1,5-trans,trans-octadienyl)phenyl]acetylene, 1-(4-methoxy-3-fluorophenyl)-2-[4-(1-trans-propenyl)-2,3-difluorophenyl]acetylene, 1-(4-cyano-3,5-difluorophenyl)-2-[4-(1-trans-pentenyl)phenyl]acetylene, 1-[4-(4-propylcyclohexyl)phenyl]-2-[4-(1-trans-propenyl)-2-fluorophenyl]acetylene, 1-[4-(4-propylcyclohexyl)phenyl]-2-[4-(trans-pentenyl)-2,6-difluorophenyl]acetylene, 1-(2-decyloxypyridin-5-yl)-2-[4-(1-trans-nonenyl)phenyl]acetylene, 1-(2-decyloxypyrimidin-5-yl)-2-[4-(1-trans-nonenyl)phenyl]acetylene, 1-(3,4-difluorophenyl)-2-[4-(1-trans-pentenyl)-2-fluorophenyl]acetylene, 1-(4-cyanophenyl)-2-[4-(1-trans-pentenyl)-2-fluorophenyl]acetylene, 1-(4-fluorophenyl)-2-[4-(1-trans-pentenyl)-2-fluorophenyl]acetylene, 1-(4-cyano-3-fluorophenyl)-2-[4-(1-trans-heptenyl)-2-fluorophenyl]acetylene, 1-(4-propylphenyl)-2-[4-(1-trans-pentenyl)-2-fluorophenyl]acetylene, 1-(4-cyanophenyl)-2-[4-(1-trans-heptenyl)phenyl]acetylene, 1-(4-cyanophenyl)-2-[4-(1-trans-butenyl)phenyl]acetylene, 1-(3,4-difluorophenyl)-2-[4-(1-trans-pentenyl)-2-fluorophenyl]acetylene, 1-(4-trifluoromethoxy-3-fluorophenyl)-2-[4-(1-trans-heptenyl)phenyl]acetylene, 1-(4-methylphenyl)-2-[4-(1-trans-pentenyl)-2,3-difluorophenyl]acetylene, 1-[4-(4-propylcyclohexyl)phenyl)-2-[4-(1-trans-propenyl)phenyl]acetylene, 1-(4-propylphenyl)-2-[4-[1-trans-(3-ethoxy)propenyl]-2-fluorophenyl]acetylene, 1-(4-propyl-3-fluorophenyl)-2-[4-(1-trans-pentenyl)phenyl]acetylene, 1-(4-methoxyphenyl)-2-[4-(1-trans-heptenyl)phenyl]acetylene, 1-[4-(1-pentynyl)-3-fluorophenyl]-2-[4-(1-trans-pentenyl)-3-fluorophenyl]acetylene, 1-(4-decyloxy-2,3-difluorophenyl)-2-[4-(1-trans-heptenyl)phenyl]acetylene, 1-(3,4-difluorophenyl)-2-[4-(1-trans-butenyl)phenyl]acetylene, 1-(4-trifluoromethoxyphenyl)-2-[4-(1-trans-hexenyl)-2-fluorophenyl]acetylene, 1-(4-methyl-2-fluorophenyl)-2-[4-(1-trans-heptenyl)-2,3-difluorophenyl]acetylene, 1-[4-(2-butenyloxy)phenyl]-2-[4-(1-trans-pentenyl)phenyl]acetylene, 1-[4-(4-propylcyclohexyl)phenyl-2-[4-(1-trans-butenyl)-3-fluorophenyl]acetylene, 1-(4-propylphenyl)-2-[5-(1-trans-pentenyl)pyrimidin-2-yl]acetylene, 1-(2-butylpyrimidin-5-yl)-2-[4-(1-trans-butenyl)-2-fluorophenyl]acetylene, 1-(4-cyanophenyl)-2-[5-(1-trans-butenyl)pyrimidin-2-yl]acetylene, 1-(4-cyanophenyl)-2-[5-(1-trans-pentenyl)pyrimidin-2-yl]acetylene, 1-(2-ethoxypyrimidin-5-yl)-2-[4-(1-trans-pentenyl)phenyl]acetylene, 1-(4-butylphenyl)-2-[5-(1-trans-pentenyl)pyrazin-2-yl]acetylene, 1-(4-methoxyphenyl)-2-[5-(1-trans-heptenyl)pyrazin-2-yl]acetylene, 1-(4-methoxy-2,3-difluorophenyl)-2-[2-(1-trans-pentenyl)pyridin-5-yl]acetylene, 1-(4-trifluoromethoxyphenyl)-2-[5-(1-trans-butenyl)pyrimidin-2-yl]acetylene, 1-(2-ethoxypyridin-5-yl)-2-[5-(1-trans-pentenyl)pyrimidin-2-yl]acetylene, 1-(3-decylpyridazin-6-yl)-2-[4-(1-trans-pentenyl)phenyl]acetylene, 1-[4-(4-propylcyclohexyl)phenyl]-2-[5-(trans-pentenyl)pyrimidin-2-yl]acetylene, 1-[4-(4-propylcyclohexyl)phenyl]-2-[2-(trans-butenyl)pyrimidin-5-yl]acetylene, 1-[4-(4-pentylcyclohexyl)-2-fluorophenyl]-2-[2-(trans-pentenyl)pyridin-5-yl]acetylene, 1-(5-ethoxypyrimidin-2-yl)-2-[4-(1-trans-pentenyl)-2-fluorophenyl]acetylene, 1-(3,4,5-trifluorophenyl-2-[5-(trans-heptenyl)pyrimidin-2-yl]acetylene, 1-(2-ethoxypyrimidin-5-yl)-2-[5-(trans-pentenyl)pyridin-2-yl]acetylene, 1-(2-cyanopyrimidin-5-yl)-2-[4-(1-trans-pentenyl)phenyl]acetylene.

What is claimed is:

1. A diphenylacetylene compound of the formula [1]:

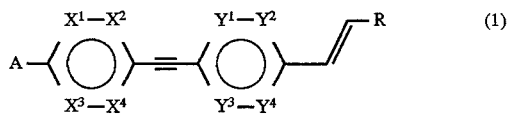

wherein R is a $C_1$–$C_{12}$ alkyl group, a $C_2$–$C_{12}$ alkenyl group or a $C_{2-C16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom;

A is a hydrogen atom, a fluorine atom, a trifluoromethyl group, a trifluoromethoxy group, a cyano group, a 4-$R^1$($C_3$–$C_8$ cycloalkyl) group, 4-$R^1$-($C_3$–$C_8$ cycloalkenyl) group or a $R^1$—(O)$_m$ group in which $R^1$ is a $C_1$–$C_{12}$ alkyl group, a $C_2$–$C_{12}$ alkenyl group or a $C_2$–$C_{12}$ alkynyl group; and m is 0 or 1.

2. The diphenylacetylene compound according to claim 1, wherein $X^1$, $X^2$, $X^3$, $X^4$, $Y^1$, $Y^2$, $Y^3$ and $Y^4$ are each a —CH— group or a —CF group, provided that at least one of $X^1$, $X^2$, $X^3$ and $X^4$ is a —CH— group, and at least one of $Y^1$, $Y^2$, $Y^3$ and $Y^4$ is a —CH— group.

3. The diphenylacetylene compound according to claim 2, wherein A is a $C_1$–$C_5$ alkyl group, R is a $C_1$–$C_5$ alkyl group, $X^1$, $X^3$, $X^4$, $Y^3$ and $Y^4$ are —CH— groups, and $X^2$, $Y^1$ and $Y^2$ are —CH— groups or —CF— groups.

4. The diphenylacetylene compound according to claim 2, wherein A is a cyano group, R is a $C_1$–$C_5$ alkyl group, $X^2$, $X^4$, $Y^2$, $Y^3$ and $Y^4$ are —CH— groups, and $X^1$, $X^3$ and $Y^1$ are —CH— groups or —CF— groups.

5. The diphenylacetylene compound according to claim 2, wherein A is a 4-$R^1$-(cycloalkyl) group, $X^1$, $X^2$, $X^3$, $X^4$, $Y^3$ and $Y^4$ are —CH— groups, and $Y^1$ and $Y^2$ are —CH— groups or —CF— groups.

6. The diphenylacetylene compound according to claim 2, wherein A is a fluorine atom or a trifluoromethoxy group, $X^2$, $X^4$, $Y^1$, $Y^2$, $Y^3$ and $Y^4$ are —CH— groups, and $X^1$ and $X^3$ are —CH— groups or —CF— groups.

7. The diphenylacetylene compound according to claim 1, wherein one of $X^1$ to $X^4$ is a nitrogen atom.

8. The diphenylacetylene compound according to claim 1, wherein one of $Y^1$ to $Y^4$ is a nitrogen atom.

9. The diphenylacetylene compound according to claim 1, wherein $X^1$ and $X^3$ are nitrogen atoms, or $X^2$ and $X^4$ is a nitrogen atom.

10. The diphenylacetylene compound according to claim 1, wherein $Y^1$ and $Y^3$ are nitrogen atoms, or $Y^2$ and $Y^4$ is a nitrogen atom.

11. A liquid crystal composition comprising a diphenylacetylene compound of the formula [1]:

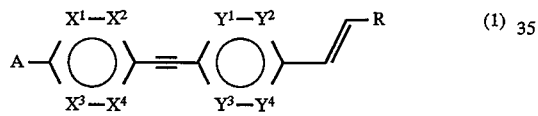

wherein R is a $C_1$–$C_{12}$ alkyl group, a $C_2$–$C_{12}$ alkenyl group or a $C_2$–$C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom;

A is a hydrogen atom, a fluorine atom, a trifluoromethyl group, a trifluoromethoxy group, a cyano group, a 4-$R^1$-($C_3$–$C_8$ cycloalkyl) group, 4-$R^1$-($C_3$–$C_8$ cycloalkenyl) group or a $R^1$—(O)$_m$ group in which $R^1$ is a $C_1$–$C_{12}$ alkyl group, a $C_2$–$C_{12}$ alkenyl group or a $C_2$–$C_{12}$ alkynyl group; and m is 0 or 1.

12. A liquid crystal element comprising the liquid crystal composition according to claim 11.

13. A process for preparing a diphenylacetylene compound of the formula (1):

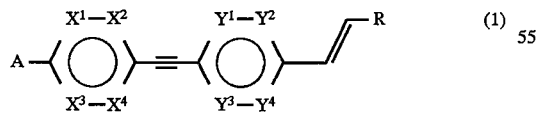

wherein R is a $C_1$–$C_{12}$ alkyl group, a $C_2$–$C_{12}$ alkenyl group or a $C_2$–$C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom; A is a hydrogen atom, a fluorine atom, a trifluoromethyl group, a 4-$R^1$-($C_3$–$C_8$ cycloalkyl) group, a 4-$R^1$-($C_3$–$C_8$ cycloalkenyl) group or a $R^1$—(O)$_m$ group in which $R^1$ is a $C_1$–$C_{12}$ alkyl group, a $C_2$–$C_{12}$ alkenyl group or a $C_2$–$C_{12}$ alkynyl group; and m is 0 or 1;

comprising reacting an aromatic compound of the formula (2):

wherein A, $X^1$, $X^2$, $X^3$, $X^4$, $Y^1$, $Y^2$, $Y^3$ and $Y^4$ are the same as defined above, and D is a halogen atom or —OSO$_2$R' in which R' is a $C_1$–$C_5$ alkyl group which may be substituted by a fluorine atom or an alkyl-, alkoxy-, or halogen-substituted or unsubstituted phenyl group;

with an ethynyl aromatic derivative of the formula (3);

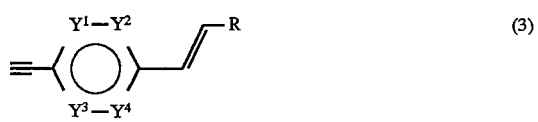

wherein R, $Y^1$, $Y^2$, $Y^3$ and $Y^4$ are the same as defined above and wherein said ethynyl aromatic derivative is prepared by treating a carbinol derivative of the formula (7):

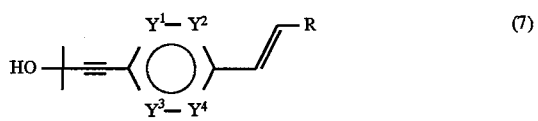

wherein R, $Y^1$, $Y^2$, $Y^3$ and $Y^4$ are the same as defined above, with a base;

wherein said carbinol derivative of the formula (7) is prepared by reacting a carbinol derivative of the formula (5):

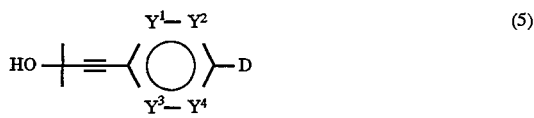

wherein D, $Y^1$, $Y^2$, $Y^3$, and $Y^4$ are the same as defined above, with a boron compound of the formula (6):

(R$^5$)$_2$B—CH=CH—R    (6)

(trans)

wherein R and each $R^5$ is a hydroxyl group, a $C_1$–$C_8$ straight alkyl group, a $C_2$–$C_8$ branched alkyl group, a $C_3$–$C_8$ cycloalkyl group, a $C_1$–$C_8$ straight alkyoxy group, a $C_2$–$C_8$ branched alkoxy group, a $C_3$–$C_8$ cycloalkoxy group, or the two $R^5$ groups together form a $C_1$–$C_8$ straight alkylene group, a $C_2$–$C_8$ branched alkylene group, a $C_3$–$C_8$ cycloalkylene group, a $C_1$–$C_8$ straight alkylenedioxy group, a $C_2$–$C_8$ branched alkylenedioxy group, a $C_3$–$C_8$ cyclic alkylenedioxy group or a benzodioxy group, in the presence of a metal catalyst and a base;

in the presence of a metal catalyst and a base.

14. The process according to claim 13, wherein said metal catalyst is at least one catalyst selected from the group consisting of palladium catalysts, nickel catalysts, rhodium catalysts and copper catalysts, and said base is at least one compound selected from the group consisting of carbonates, carboxylic acid salts, alkoxides and hydroxides of alkali metals and organic bases.

15. A process for preparing a diphenylacetylene compound of the formula (1):

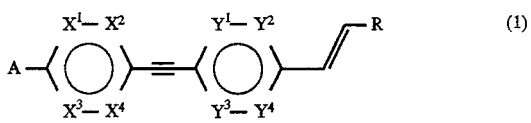

(1)

wherein R is a $C_1$–$C_{12}$ alkyl group, a $C_2$–$C_{12}$ alkenyl group or a $C_2$–$C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom; A is a hydrogen atom, a fluorine atom, a trifluoromethyl group, a trifluoromethoxy group, a cyano group, a 4-$R^1$-($C_3$–$C_8$ cycloalkyl) group, a 4-$R^1$-($C_3$–$C_8$ cycloalkenyl) group or a $R^1$—(O)$_m$ group in which $R^1$ is a $C_1$–$C_{12}$ alkyl group, a $C_2$–$C_{12}$ alkenyl group or a $C_2$–$C_{12}$ alkynyl group; and m is 0 or 1;

comprising reacting a diphenylacetylene derivative of the formula (10):

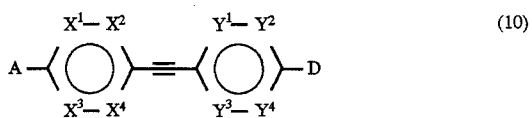

(10)

wherein A, $X^1$, $X^2$, $X^3$, $X^4$, $Y^1$, $Y^2$, $Y^3$ and $Y^4$ are the same as defined above, and D is a halogen atom or —OSO$_2$R' in which R' is a $C_1$–$C_5$ alkyl group which may be substituted by a fluorine atom or an alkyl-, alkoxy-, or halogen-substituted or unsubstituted phenyl group with a boron compound of the formula (6):

(6)

(trans)

wherein R is the same as defined above and each $R^5$ is a hydroxyl group, a $C_1$–$C_8$ straight alkyl group, a $C_2$–$C_8$ branched alkyl group, a $C_3$–$C_8$ cycloalkyl group, a $C_1$–$C_8$ straight alkyoxy group, a $C_2$–$C_8$ branched alkoxy group, a $C_3$–$C_8$ cycloalkoxy group, or the two $R^5$ groups together form a $C_1$–$C_8$ straight alkylene group, a $C_2$–$C_8$ branched alkylene group, a $C_3$–$C_8$ cycloalkylene group, a $C_1$–$C_8$ straight alkylenedioxy group, a $C_2$–$C_8$ branched alkylenedioxy group, a $C_3$–$C_8$ cyclic alkylenedioxy group or a benzodioxy group;

in the presence of a metal catalyst and a base.

16. The process according to claim 15, wherein said metal catalyst is at least one catalyst selected from the group consisting of palladium catalysts, nickel catalysts, rhodium catalysts and copper catalysts, and said base is at least one compound selected from the group consisting of carbonates, carboxylic acid salts, alkoxides and hydroxides of alkali metals and organic bases.

17. A process for preparing a diphenylacetylene compound of the formula (1):

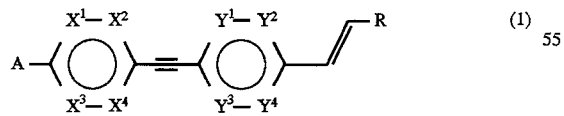

(1)

wherein R is a $C_1$–$C_{12}$ alkyl group, a $C_2$–$C_{12}$ alkenyl group or a $C_2$–$C_{16}$ alkoxyalkyl group; $X^1$, $X^2$, $X^3$, $X^4$, $Y^1$, $Y^2$, $Y^3$ and $Y^4$ are independently from each other a —CH— group, a —CF— group or a nitrogen atom; A is a hydrogen atom, a fluorine atom, a trifluoromethyl group, a trifluoromethoxy group, a cyano group, a 4-$R^1$-($C_3$–$C_8$ cycloalkyl) group, a 4-$R^1$-($C_3$–$C_8$ cycloalkenyl) group or a $R^1$—(O)$_m$ group in which $R^1$ is a $C_1$–$C_{12}$ alkyl group, a $C_2$–$C_{12}$ alkenyl group or a $C_2$–$C_{12}$ alkynyl group; and m is 0 or 1:

comprising reacting an ethynyl aromatic compound of the formula (11):

(11)

wherein A, $X^1$, $X^2$, $X^3$, and $X^4$, are the same as defined above;

wherein said ethynyl aromatic compound (11) is synthesized by a process:

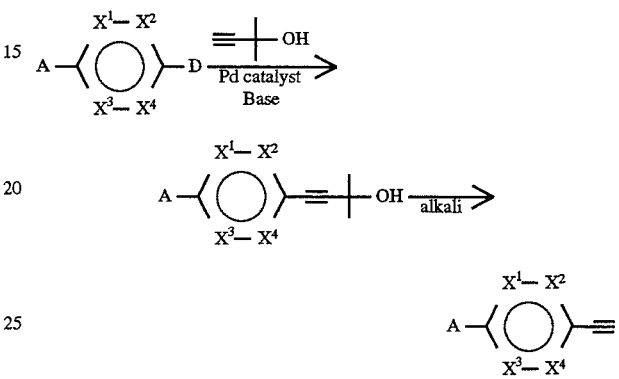

with an aromatic derivative of the formula (12):

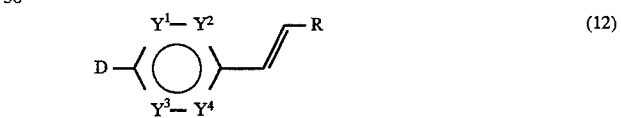

(12)

wherein R, $Y^1$, $Y^2$, $Y^3$ and $Y^4$ are the same as defined above, and D is a halogen atom or —OSO$_2$R' in which R' is a $C_1$–$C_5$ alkyl group which may be substituted by a fluorine atom or an alkyl-, alkoxy-, or halogen-substituted or unsubstituted phenyl group;

wherein said aromatic derivative of the formula (12) is synthesized by a process:

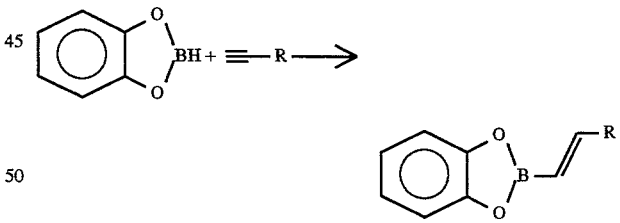

(1) when D is a halogen atom:

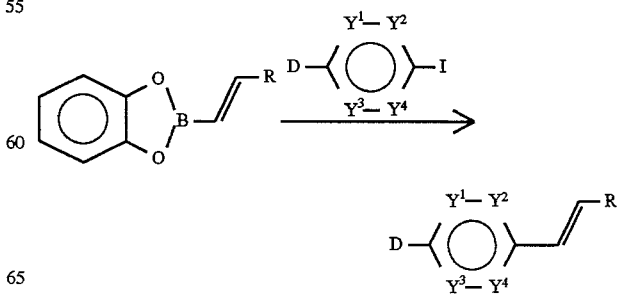

(2) when D is —OSO₂R:

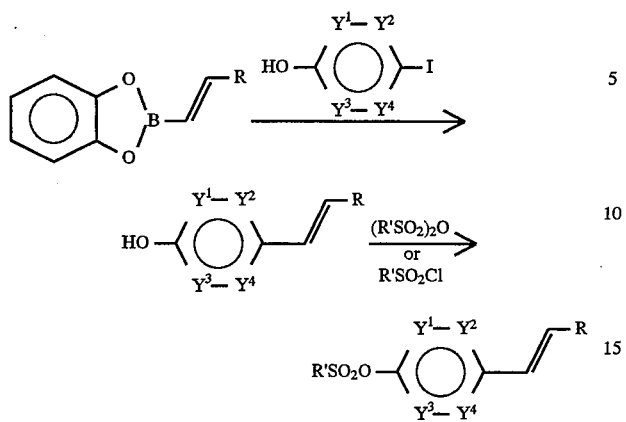

in the presence of a metal catalyst and a base.

18. The process according to claim 17, wherein said metal catalyst is at least one catalyst selected from the consisting of palladium catalysts, nickel catalysts, rhodium catalysts and copper catalysts, and said base is at least one compound selected from the group consisting of carbonates, carboxylic acid salts, alkoxides and hydroxides of alkali metals and organic bases.

19. A process for preparing 1-(4-(1-trans-pentenyl) phenyl)acetylene, comprising:

reacting 4-cyano-1-trifluoromethanesulfonyloxybenzene, 4-(1-trans-pentenyl)phenylacetylene and bis (triphenylphosphine)palladium chloride with a metal catalyst and a base.

20. The process of claim 19, wherein said metal catalyst is cuprous iodide and said base consists essentially of triethylamine and N-methyl-piperazine.

* * * * *